US006864241B2

United States Patent
Takechi

(10) Patent No.: US 6,864,241 B2
(45) Date of Patent: Mar. 8, 2005

(54) AMINE SALT OF LIGNAN COMPOUNDS

(75) Inventor: Shozo Takechi, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 199 days.

(21) Appl. No.: 10/312,617

(22) PCT Filed: Jun. 19, 2001

(86) PCT No.: PCT/JP01/05194

§ 371 (c)(1),
(2), (4) Date: Dec. 27, 2002

(87) PCT Pub. No.: WO02/02583

PCT Pub. Date: Jan. 10, 2002

(65) Prior Publication Data

US 2003/0119758 A1 Jun. 26, 2003

(30) Foreign Application Priority Data

Jun. 30, 2000 (JP) ........................................ 2000-198043

(51) Int. Cl.$^7$ ................. A61K 31/704; A61K 31/7028; C07H 15/04
(52) U.S. Cl. ........................... 514/25; 536/4.1; 536/18.2
(58) Field of Search ............................. 514/25; 536/4.1, 536/18.2

(56) References Cited

FOREIGN PATENT DOCUMENTS

| JP | 9-241206 | | 9/1997 |
|---|---|---|---|
| JP | 09241206 | * | 9/1997 |

OTHER PUBLICATIONS

Yamaguchi et al., Arzneimittel–Forschung (1998), 48 (10), 995–1006.*
Yamaguchi et al., "Disposition and Metabolism of the New Hypocholesterolemic Compound S–8921 in Rats and Dogs", Arzneim.–Forsch., vol. 48, No. 10, pp. 995–1006, 1998.

* cited by examiner

Primary Examiner—Samuel Barts
Assistant Examiner—Michael C. Henry
(74) Attorney, Agent, or Firm—Wenderoth, Lind & Ponack, L.L.P.

(57) ABSTRACT

The present invention provides an amine salt of a lignan compound, i.e., [1-O-[4-(3,4-dimethoxyphenyl)-2-(3-ethylpentanoyl)-5,6,7-trimethoxy-3-(methoxycarbonyl)naphthalen-1-yl]-beta-D-glucopyranoside]uronic acid, which is useful as a medicament. The present invention also provides a method for purifying said lignan compound.

19 Claims, No Drawings

AMINE SALT OF LIGNAN COMPOUNDS

TECHNICAL FIELD

The present invention relates to an amine salt of a lignan compound.

BACKGROUND ART

A lignan compound represented by formula I:

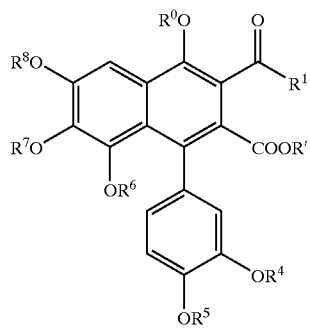

wherein, $R^0$ is a hydrogen or a hydrophilic group;

$R^1$ is a lower alkyl group which may be substituted, a cycloalkyl group which may be substituted, a cycloalkyl lower alkyl group which may be substituted, an aryl group which may be substituted, an aralkyl group which may be substituted, a heterocycle which may be substituted;

R' is a lower alkyl group which may be substituted or an aralkyl group which may be substituted; and $R^4$, $R^5$, $R^6$, $R^7$ and $R^8$ are each a lower alkyl group and salts thereof are known to be useful in various clinical uses, particularly, as an antihyperlipidemia drug or a bile acid reabsorption inhibiting drug (Japanese Patent Publication (not examined) No. 241206/1997). The present inventors have found that a lignan compound represented by the following formula II, which is a member of the above formula I, is particularly useful as a medicament. However, this compound is not crystalline, and therefore, in an industrial production thereof, it has been necessary to conduct column chromatography for several times in order to purify the compound. Moreover, the yield of the compound has been low for this reason. The above Japanese Patent Publication (not examined) No. 241206/1997 does not describe an amine salt in terms of a salt of a compound of formula I.

Problems to be Solved by the Invention

In an industrial mass production aiming at use as a medicament of the compound represented by formula II:

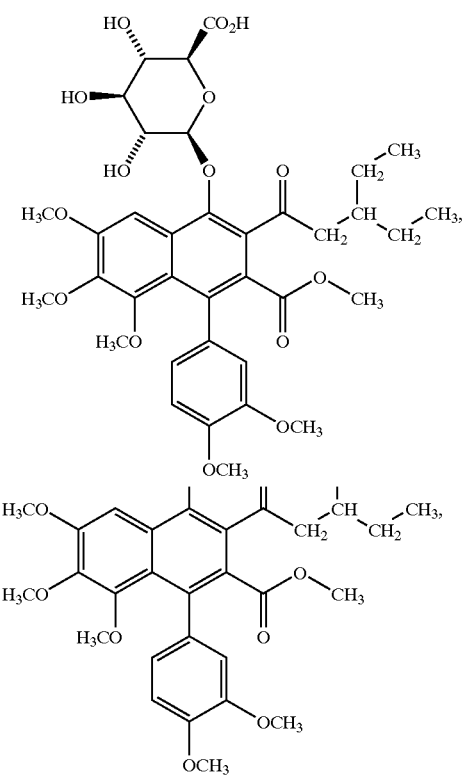

i.e., [1-O-[4-(3,4-dimethoxyphenyl)-2-(3-ethylpentanoyl)-5,6,7-trimethoxy-3-(methoxycarbonyl)naphthalen-1-yl]-beta-D-glucopyranoside]uronic acid (glucuronate conjugate), it was very inconvenient that column chromatography had to be conducted in order to purify the compound, and therefore, development of a simple method for the purification of the compound has been desired.

Means to Solve the Problems

As a result of research for the purification of the compound of formula II, the present inventors have found that this compound can be crystallized by transforming into an amine salt thereof, and here, succeeded in purifying this compound efficiently by such crystallization. The present invention has been accomplished by this discovery. By transforming into an amine salt to be crystallized, the compound of formula II can be refined and easily isolated from a reaction mixture by means such as filtration. The amine salt of said compound isolated can be transformed easily into the free compound by treating with a dilute acid or the like.

Thus, the present invention provides (1) An amine salt of [1-O-[4-(3,4-dimethoxyphenyl)-2-(3-ethylpentanoyl)-5,6,7-trimethoxy-3-(methoxycarbonyl)naphthalen-1-yl]-beta-D-glucopyranoside]uronic acid;

(2) The amine salt of (1) which is a diethylamine salt;

(3) The amine salt of (1) or (2) which is a crystal;

(4) The diethylamine salt of (3) which exhibits a powder X-ray diffraction pattern wherein the main peaks appear at 2θ=9.800, 13.760, 16.960, 17.100, 18.140 and 18.340 (degree);

(5) The diethylamine salt of (4) which exhibits a powder X-ray diffraction pattern wherein the main peaks appear at 2θ=8.820, 9.800, 13.760, 14.340, 14.540, 15.560, 16.960, 17.100, 18.140, 18.340, 19.560, 21.740, 22.040 and 22.280 (degree);

(6) A process for preparing [1-O-[4-(3,4-dimethoxyphenyl)-2-(3-ethylpentanoyl)-5,6,7-trimethoxy-3-(methoxycarbonyl)naphthalen-1-yl]-beta-D-glucopyranoside]uronic acid, which comprises purification thereof by transforming the acid into an crystalline amine salt;

(7) The process of (6) wherein said process does not comprise a treatment by means of column chromatography;

(8) A process for preparing [1-O-[4-(3,4-dimethoxyphenyl)-2-(3-ethylpentanoyl)-5,6,7-trimethoxy-3-(methoxycarbonyl)naphthalen-1-yl]-beta-D-glucopyranoside]uronic acid, which comprises a treatment of a crystalline amine salt thereof to form the free compound; and (9) A pharmaceutical composition comprising the amine salt of any one of (1)–(5).

For preparation of the amine salt of the invention, a crude product of the compound of formula (II) is dissolved in an appropriate solvent, for example, alcoholic solvents such as methanol, ethanol, or isopropyl alcohol, ether solvents such as THF, aromatic hydrocarbons such as toluene, or xylene. The resultant mixture is added with an amine to mix at a temperature between 0° C. and 100° C., preferably between room temperature and 70° C., and then optionally allowed to cool to a temperature between room temperature and 0° C. Crystals precipitated can be filtered out and washed with a solvent as described above. Diethylamine is preferable for use as an amine.

As described above, the resultant amine salt of the compound of formula II, can be treated easily with an acid, such as a dilute acid, to form the free compound.

As described above, the amine salt of the invention is useful as an intermediate, but itself may be used as an active ingredient. Accordingly, the present invention further provides a medicament, such as anti-hyperlipidemia drug, containing said amine salt. The amine salt of the invention may be a solvate, such as a hydrate or an alcoholate.

Best Mode for Carrying Out the Invention

The following examples further illustrate the present invention and are not intended to be limiting to the scope of the invention in any respect.

EXAMPLE 1

Step 1

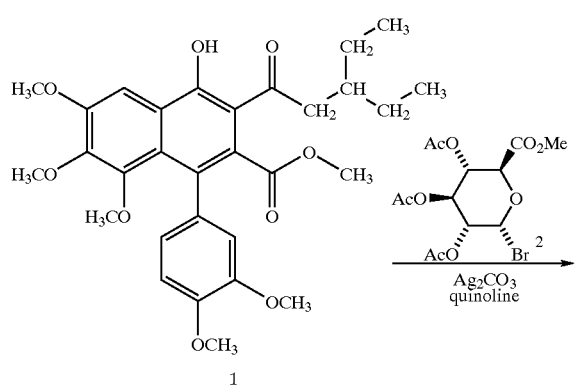

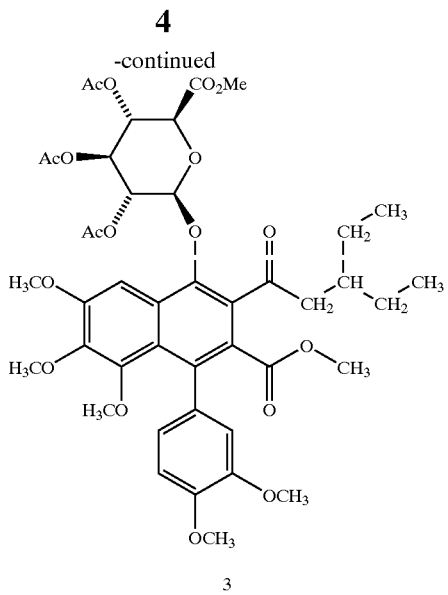

Under nitrogen stream, 2.58 g of Silver(I) Carbonate was added to a solution in quinoline (27 mL) of 3.00 g (5.56 mmol) of Compound 1, which is described in Example 1 of Japanese Patent Publication (not examined) No. 310634/1993, and the mixture was stirred for 42 minutes under room temperature. To the resultant reaction mixture, 3.53 g (8.89 mmol) of Bromide 2 was added, and the mixture was stirred for 20 hours. Then, ice, 6 N hydrochloric acid (40 mL) and ethyl acetate were added, and the mixture was filtered. The filtrate was extracted with ethyl acetate, and the extract was washed with water, saturated sodium bicarbonate solution and brine, and dried over anhydrous magnesium sulfate. The solvent was removed under reduced pressure to yield 5.0 g of a crude product of Compound 3. The resultant product was used in the next reaction without further purification.

Rf: 0.22 (n-hexane:EtOAc=1:1, SiO$_2$TLC)

Step 2

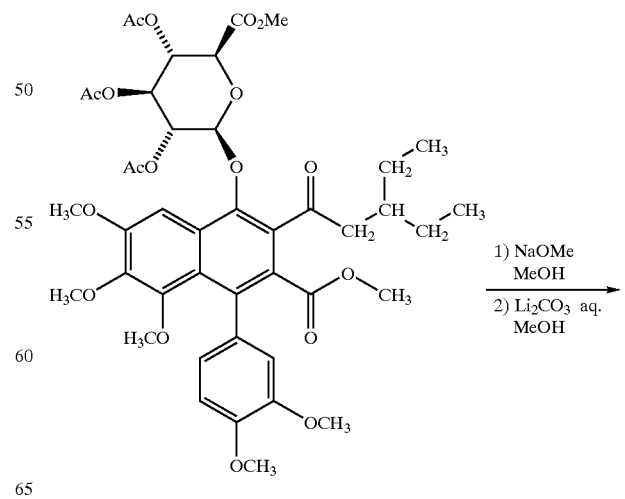

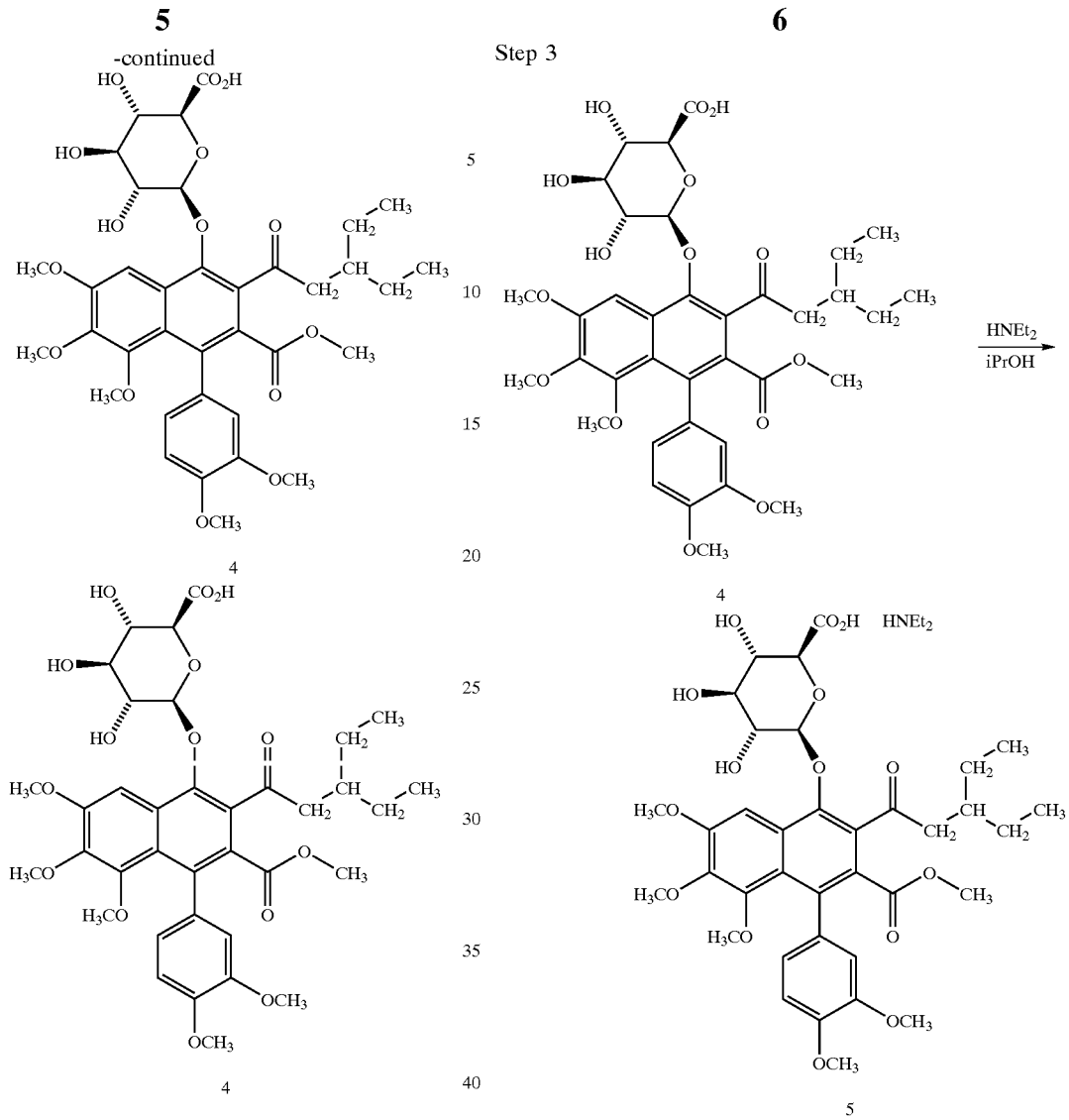

The crude product of Compound 3 obtained above (5.0 g) was dissolved in methanol (50 mL), added with 60% sodium hydride (145 mg) under ice cooling, and the resultant mixture was allowed to warm to room temperature with stirring for two hours. Saturated aqueous solution of ammonium chloride (2 mL) was added to the mixture, and methanol was removed under reduced pressure. To the residue, water was added and the mixture was extracted with ethyl acetate. The extract was washed with water and brine, and dried over anhydrous magnesium sulfate. Solvent was removed under reduced pressure to yield 4.2 g of a residue. The residue (4.2 g) was dissolved in methanol (120 mL), added with aqueous solution of lithium carbonate (prepared from. 425 mg of lithium carbonate and 60 mL of water) under ice cooling. The resultant mixture was allowed to warm to room temperature with stirring for three days. Solvent was removed under reduced pressure. To the residue, 1 N hydrochloric acid (13.5 mL) was added under ice cooling, adjusted the pH to 4, and the mixture was extracted with ethyl acetate. The extract was washed with water and brine, and dried over anhydrous magnesium sulfate. Solvent was removed under reduced pressure to yield 3.1 g of a crude product of Compound 4. The resultant product was used in the next reaction without further purification.

Rf: 0.27 (toluene:$CH_3CN$:AcOH:n-BuOH=10:10:1:1, $SiO_2$TLC)

Step 3

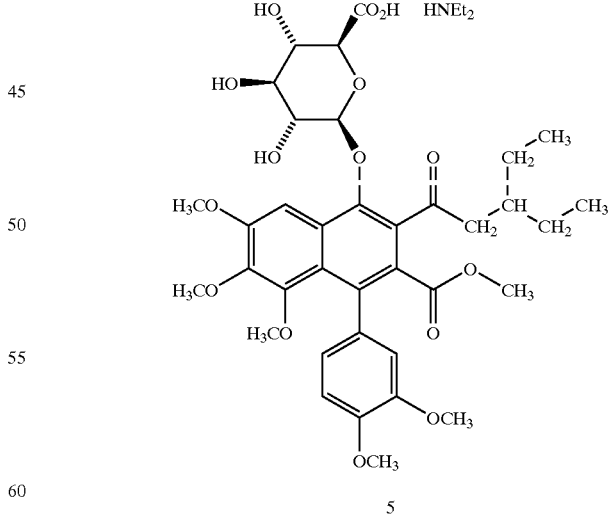

The crude product of Compound 4 obtained above (3.1 g) was dissolved in isopropyl alcohol (40 mL), and diethylamine (0.63 mL) was added to the solution at 50° C., and the resultant mixture was allowed to cool to room temperature with stirring for 1 hour. Precipitated crystals were filtered out, washed with isopropyl alcohol for three times to yield 2.57 g of the desired Compound 5 (59% in three steps). mp: 205–206° C. (dec)

$^1$H NMR: δ (DMSO-$d_6$) 0.78–0.85 (m, 6H), 1.12 (t, J=7.2 Hz, 6H), 1.21–1.38 (m, 4H), 1.78–1.84 (m, 1H), 2.83 (q, J=7.2 Hz, 4H), 2.99–3.80 (m, 22H), 3.95 (s, 3H), 4.74 (d like, 1H), 5.13 (br.s, 1H), 5.83–6.00 (m, 1H), 6.59–6.93 (m, 3H), 8.13 & 8.14 (each s, total 1H).

IR: ν (CHCl$_3$) 3587, 3170, 3008, 2964, 1722, 1682, 1608, 1516, 1464, 1414, 1352, 1240, 1138, 1066.

Anal. Calcd. for $C_{40}H_{55}NO_{15}$: C, 60.82; H, 7.02; N, 1.77: Calcd. for $C_{40}H_{55}NO_{15}$·3/10$H_2O$: C, 60.41; H, 7.05; N, 1.76.

Found: C, 60.23; H, 7.01; N, 2.04.

Karl Fisher Calcd. for $C_{40}H_{55}NO_{15}$·3/10$H_2O$: $H_2O$, 0.68. Found: $H_2O$, 0.68.

X-ray diffraction pattern of Compound 5 was as shown bellow.

TABLE 1

| 2θ | Half Value Breadth | d value | Intensity | Relative Intensity |
|---|---|---|---|---|
| 6.820 | 0.118 | 12.9501 | 80 | 7 |
| 7.340 | 0.141 | 12.0338 | 102 | 9 |
| 8.500 | 0.188 | 10.3940 | 495 | 43 |
| 8.820 | 0.259 | 10.0176 | 580 | 50 |
| 9.800 | 0.306 | 9.0179 | 982 | 85 |
| 10.200 | 0.141 | 8.6651 | 435 | 37 |
| 10.840 | 0.141 | 8.1549 | 130 | 11 |
| 11.080 | 0.118 | 7.9788 | 135 | 12 |
| 12.280 | 0.165 | 7.2017 | 230 | 20 |
| 12.840 | 0.118 | 6.8888 | 160 | 14 |
| 13.760 | 0.188 | 6.4302 | 970 | 83 |
| 14.340 | 0.141 | 6.1714 | 650 | 56 |
| 14.540 | 0.141 | 6.0870 | 695 | 60 |
| 15.360 | 0.235 | 5.7638 | 530 | 46 |
| 15.560 | 0.165 | 5.6902 | 705 | 61 |
| 16.400 | 0.118 | 5.4006 | 340 | 29 |
| 16.960 | 0.188 | 5.2235 | 1005 | 86 |
| 17.100 | 0.259 | 5.1811 | 1092 | 94 |
| 18.140 | 0.235 | 4.8863 | 1162 | 100 |
| 18.340 | 0.141 | 4.8335 | 982 | 85 |
| 18.740 | 0.118 | 4.7312 | 492 | 42 |
| 19.560 | 0.165 | 4.5347 | 678 | 58 |
| 20.200 | 0.118 | 4.3924 | 320 | 28 |
| 21.140 | 0.118 | 4.1992 | 382 | 33 |
| 21.740 | 0.118 | 4.0846 | 625 | 54 |
| 22.040 | 0.141 | 4.0297 | 675 | 58 |
| 22.280 | 0.212 | 3.9868 | 632 | 54 |
| 23.560 | 0.141 | 3.7730 | 382 | 33 |
| 24.140 | 0.141 | 3.6837 | 415 | 36 |
| 24.360 | 0.118 | 3.6509 | 282 | 24 |
| 25.420 | 0.118 | 3.5010 | 288 | 25 |
| 25.680 | 0.141 | 3.4662 | 270 | 23 |
| 25.840 | 0.118 | 3.4451 | 282 | 24 |
| 26.840 | 0.118 | 3.3189 | 298 | 26 |
| 27.060 | 0.118 | 3.2924 | 308 | 26 |
| 27.700 | 0.141 | 3.2178 | 280 | 24 |
| 27.880 | 0.141 | 3.1974 | 268 | 23 |
| 28.160 | 0.141 | 3.1663 | 288 | 25 |
| 28.380 | 0.165 | 3.1422 | 205 | 18 |
| 28.760 | 0.118 | 3.1016 | 268 | 23 |
| 29.120 | 0.118 | 3.0640 | 308 | 26 |
| 29.260 | 0.118 | 3.0497 | 362 | 31 |
| 29.680 | 0.118 | 3.0075 | 242 | 21 |
| 31.220 | 0.165 | 2.8626 | 248 | 21 |
| 32.020 | 0.118 | 2.7928 | 230 | 20 |
| 33.160 | 0.118 | 2.6994 | 200 | 17 |
| 38.380 | 0.141 | 2.3434 | 225 | 19 |
| 38.520 | 0.118 | 2.3352 | 135 | 12 |

Conditions for the X-ray diffraction analysis
Model: RIGAKU DENKISYA RAD-IIC Powder X-ray Diffraction meter X-ray: CuK-ALPHA1/40 kV/40 mM
Goniometer: wide-angle goniometer
Attachment: rotating stage (reflection method)
Filter: none
Counter monochrome meter: curved crystal monochrome meter
Divergence slit: 0.5°
Scattering slit: 0.5°
Receiving slit: 0.3 mm
Counter: scintillation counter
Scanning mode: continuous
Scanning speed: 3°/min
Scanning step: 0.02°
Scanning axis: 2θ/θ
Scanning range: 5–40°
θ offset: 0°
Fixed angle: 0°
Cuvette: 5 mm Φ

Step 4

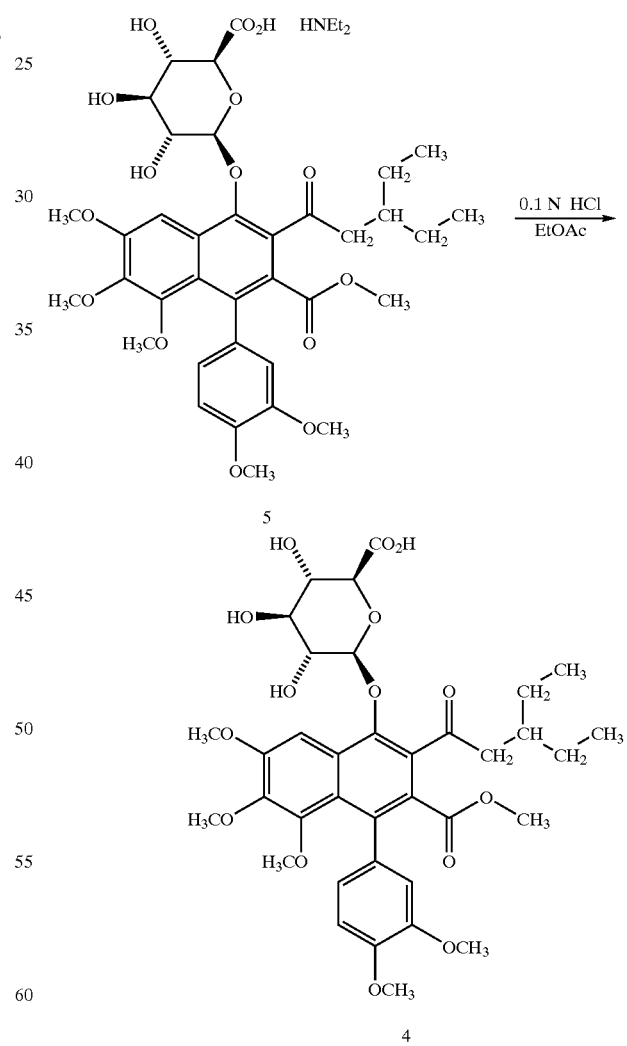

Compound 5 obtained above (1.00 g, 12.7 mmol) was added with ethyl acetate (30 mL) and water (30 mL), and the pH was adjusted to 4.0 by addition of 0.1 N hydrochloric acid. The reaction mixture was extracted with ethyl acetate, washed with saturated aqueous solution of sodium chloride, and dried over anhydrous sodium sulfate. Solvent was removed under reduced pressure, and the resultant residue was dissolved in ether (40 mL), and solvent was removed again under reduced pressure. The residue was powdered from ether/n-pentane to give 806 mg (87%) of the desired Compound 4 as an amorphous material.

$^1$HNMR: δ (DMSO-d$_6$) 0.81 (t, J=7.5 Hz, 3H), 0.88 (t, J=7.5 Hz, 3H), 1.18–1.41 (m, 4H), 1.78–1.89 (m, 1H), 2.69–2.80 (m, 1H), 3.17–3.80 (m, 20H), 3.96 (s, 3H), 4.71 (t like, 1H), 5.34 (br.s, 1H), 5.36 (d like, 1H), 6.19 & 6.23 (each d, J=5.1 Hz, total 1H), 6.57–6.95 (m, 3H), 8.17 (s, 1H), 12.60 (br.s, 1H).

IR: ν (CHCl$_3$), 3591, 3483, 3327, 2964, 1743, 1697, 1608, 1516, 1464, 1415, 1352, 1242, 1138, 1095, 1065, 1030.

Reference Example 1

X-ray diffraction pattern of Compound 1 was as shown bellow. The conditions used were the same as in Example 1.

TABLE 2

| 2θ | Half Value Breadth | d value | Intensity | Relative Intensity |
|---|---|---|---|---|
| 6.520 | 0.165 | 13.5453 | 392 | 21 |
| 7.360 | 0.165 | 12.0011 | 1780 | 96 |
| 10.540 | 0.282 | 8.3864 | 555 | 30 |
| 12.060 | 0.212 | 7.3326 | 1338 | 72 |
| 12.400 | 0.188 | 7.1323 | 540 | 29 |
| 13.080 | 0.235 | 6.7630 | 338 | 18 |
| 14.580 | 0.118 | 6.0704 | 212 | 12 |
| 15.060 | 0.329 | 5.8780 | 335 | 18 |
| 16.340 | 0.188 | 5.4203 | 635 | 34 |
| 17.560 | 0.141 | 5.0464 | 358 | 19 |
| 18.260 | 0.212 | 4.8545 | 372 | 20 |
| 19.740 | 0.165 | 4.4937 | 478 | 26 |
| 20.960 | 0.165 | 4.2348 | 295 | 16 |
| 21.640 | 0.118 | 4.1033 | 548 | 30 |
| 22.280 | 0.235 | 3.9868 | 412 | 22 |
| 22.940 | 0.212 | 3.8736 | 1845 | 100 |
| 23.480 | 0.212 | 3.7857 | 752 | 41 |
| 24.380 | 0.212 | 3.6480 | 1292 | 70 |
| 25.880 | 0.118 | 3.4398 | 410 | 22 |
| 26.260 | 0.259 | 3.3909 | 355 | 19 |
| 26.600 | 0.118 | 3.3483 | 218 | 12 |
| 26.700 | 0.118 | 3.3360 | 185 | 10 |
| 27.040 | 0.118 | 3.2948 | 245 | 13 |
| 27.140 | 0.118 | 3.2829 | 220 | 12 |
| 27.460 | 0.165 | 3.2454 | 170 | 9 |
| 28.240 | 0.188 | 3.1575 | 380 | 21 |
| 28.500 | 0.165 | 3.1293 | 290 | 16 |
| 28.940 | 0.141 | 3.0827 | 148 | 8 |
| 29.460 | 0.165 | 3.0294 | 302 | 16 |
| 30.020 | 0.141 | 2.9742 | 128 | 7 |
| 30.980 | 0.141 | 2.8842 | 190 | 10 |
| 31.160 | 0.118 | 2.8679 | 165 | 9 |
| 31.780 | 0.118 | 2.8134 | 182 | 10 |
| 32.620 | 0.118 | 2.8134 | 178 | 10 |
| 38.420 | 0.212 | 2.3411 | 470 | 25 |
| 39.060 | 0.141 | 2.3042 | 128 | 7 |

Effect of the Invention

The present invention enables simple purification of the compound which is useful as a medicament, i.e., [1-O-[4-(3,4-dimethoxyphenyl)-2-(3-ethylpentanoyl)-5,6,7-trimethoxy-3-(methoxycarbonyl)naphthalen-1-yl]-beta-D-glucopyranoside]uronic acid, by transforming said compound into an amine salt thereof to be crystallized, and thus has opened the way to use this compound as a medicament. Furthermore, the present invention has improved drastically the total yield of this compound from Compound 1.

What is claimed is:

1. An amine salt of [1-O-[4-(3,4-dimethoxyphenyl)-2-(3-ethylpentanoyl)-5,6,7-trimethoxy-3-(methoxycarbonyl)naphthalen-1-yl]-beta-D-glucopyranoside]uronic acid.

2. The amine salt of claim 1 which is a diethylamine salt.

3. The amine salt of claim 1 which is a crystal.

4. The diethylamine salt of claim 3, which exhibits a powder X-ray diffraction pattern wherein the main peaks appear at 2θ=9.800, 13.760, 16.960, 17.100, 18.140 and 18.340 (degree).

5. The diethylamine salt of claim 4, which exhibits a powder X-ray diffraction pattern wherein the main peaks appear at 2θ=8.820, 9.800, 13.760, 14.340, 14.540, 15.560, 16.960, 17.100, 18.140, 18.340, 19.560, 21.740, 22.040 and 22.280 (degree).

6. A process for preparing [1-O-[4-(3,4-dimethoxyphenyl)-2-(3-ethylpentanoyl)-5,6,7-trimethoxy-3-(methoxycarbonyl)naphthalen-1-yl]-beta-D-glucopyranoside]uronic acid, which comprises purification thereof by transforming the acid into an crystalline amine salt.

7. The process of claim 6, wherein said process does not comprise a treatment by means of column chromatography.

8. A process for preparing [1-O-[4-(3,4-dimethoxyphenyl)-2-(3-ethylpentanoyl)-5,6,7-trimethoxy-3-(methoxycarbonyl)naphthalen-1-yl]-beta-D-glucopyranoside]uronic acid, which comprises a treatment of a crystalline amine salt thereof to form the free compound.

9. A pharmaceutical composition comprising the amine salt of claim 1.

10. The amine salt of claim 2 which is a crystal.

11. The diethylamine salt of claim 10, which exhibits a powder X-ray diffraction pattern wherein the main peaks appear at 2θ=9.800, 13.760, 16.960, 17.100, 18.140 and 18.340 (degree).

12. The diethylamine salt of claim 11, which exhibits a powder X-ray diffraction pattern wherein the main peaks appear at 2θ=8.820, 9.800, 13.760, 14.340, 14.540, 15.560, 16.960, 17.100, 18.140, 18.340, 19.560, 21.740, 22.040 and 22.280 (degree).

13. A pharmaceutical composition comprising the amine salt of claim 2.

14. A pharmaceutical composition comprising the amine salt of claim 3.

15. A pharmaceutical composition comprising the amine salt of claim 4.

16. A pharmaceutical composition comprising the amine salt of claim 5.

17. A pharmaceutical composition comprising the amine salt of claim 10.

18. A pharmaceutical composition comprising the amine salt of claim 11.

19. A pharmaceutical composition comprising the amine salt of claim 12.

* * * * *